United States Patent
Davis et al.

(10) Patent No.: US 6,962,488 B2
(45) Date of Patent: Nov. 8, 2005

(54) SURGICAL CASSETTE HAVING AN ASPIRATION PRESSURE SENSOR

(75) Inventors: Sherman G. Davis, Laguna Nigel, CA (US); Raphael Gordon, San Dimas, CA (US); Valentine P. Injev, Irvine, CA (US); Kurt D. Leukanech, Laguna Nigel, CA (US); Michael D. Morgan, Costa Mesa, CA (US); Mel M. Oliveira, Huntington Beach, CA (US); Gary P. Sorensen, Lake Forest, CA (US); Daniel J. Wilson, Quali Valley, CA (US)

(73) Assignee: Alcon, Inc., Hunenberg (CH)

( * ) Notice: Subject to any disclaimer, the term of this patent is extended or adjusted under 35 U.S.C. 154(b) by 325 days.

(21) Appl. No.: 10/407,388

(22) Filed: Apr. 4, 2003

(65) Prior Publication Data
US 2003/0190244 A1  Oct. 9, 2003

Related U.S. Application Data (63) Continuation-in-part of application No. 10/153,371, filed on May 28, 2002, now Pat. No. 6,902,542, which is a continuation-in-part of application No. 09/846,724, filed on May 1, 2001, now Pat. No. 6,572,349, which is a continuation of application No. 09/437,392, filed on Nov. 10, 1999, now Pat. No. 6,293,926.

(51) Int. Cl.[7] .................. F04B 43/08; A51M 01/00; A51M 05/00

(52) U.S. Cl. ................. 417/477.2; 417/477.5; 604/153; 604/250

(58) Field of Search .................. 417/477.2, 476, 417/477.5, 477.8; 604/153, 250

(56) References Cited

U.S. PATENT DOCUMENTS

| | | | |
|---|---|---|---|
| 4,140,118 A | | 2/1979 | Jassawalla |
| 4,187,057 A | | 2/1980 | Xanthopoulos |
| 4,479,761 A | | 10/1984 | Bilstad et al. |
| 4,493,706 A | | 1/1985 | Borsanyi et al. |
| 4,530,647 A | | 7/1985 | Uno |
| 4,537,561 A | | 8/1985 | Xanthopoulos |
| 4,713,051 A | | 12/1987 | Steppe et al. |
| 4,758,238 A | | 7/1988 | Sundblom et al. |
| 4,768,547 A | | 9/1988 | Danby et al. |
| 4,795,440 A | * | 1/1989 | Young et al. ............. 604/122 |
| 4,798,090 A | * | 1/1989 | Heath et al. ............... 73/715 |
| 4,798,580 A | | 1/1989 | DeMeo et al. |
| 4,838,865 A | | 6/1989 | Flank et al. |
| 4,861,242 A | | 8/1989 | Finsterwald |
| 4,921,477 A | | 5/1990 | Davis |
| 4,923,375 A | | 5/1990 | Ejlersen |
| 4,935,005 A | | 6/1990 | Haines |
| 4,963,131 A | | 10/1990 | Wortrich |
| 5,041,096 A | | 8/1991 | Beuchat et al. |
| 5,056,992 A | * | 10/1991 | Simons et al. ............ 417/474 |

(Continued)

FOREIGN PATENT DOCUMENTS

FR    2 466 641    4/1981

*Primary Examiner*—Timothy P. Solak
(74) *Attorney, Agent, or Firm*—Jeffrey S. Schira (57) ABSTRACT

A cassette having a molded flow channel contained on an elastomeric sheet that is bonded or mechanically attached to a rigid substrate. The flow channel projects outwardly from the exterior of the cassette so that a peristaltic pump having pump head rollers mounted radially from the axis of rotation of the pump motor compress the elastomeric flow channels against the rigid substrate during operation.

44 Claims, 7 Drawing Sheets

U.S. PATENT DOCUMENTS

| | | |
|---|---|---|
| 5,106,366 A | 4/1992 | Steppe |
| 5,195,960 A | 3/1993 | Hossain et al. |
| 5,207,647 A | 5/1993 | Phelps |
| 5,267,956 A | 12/1993 | Beuchat |
| 5,302,093 A * | 4/1994 | Owens et al. ............... 417/474 |
| 5,364,342 A | 11/1994 | Beuchat et al. |
| 5,403,277 A | 4/1995 | Dodge et al. |
| 5,429,485 A | 7/1995 | Dodge |
| 5,429,602 A | 7/1995 | Hauser |
| 5,460,490 A | 10/1995 | Carr et al. |
| 5,470,312 A | 11/1995 | Zanger et al. |
| 5,518,378 A | 5/1996 | Neftel et al. |
| 5,588,815 A | 12/1996 | Zaleski, II |
| 5,709,539 A | 1/1998 | Hammer et al. |
| 5,746,708 A | 5/1998 | Giesler et al. |
| 5,746,719 A * | 5/1998 | Farra et al. .................. 604/151 |
| 5,759,017 A | 6/1998 | Patton et al. |
| 5,897,524 A * | 4/1999 | Wortrich et al. .............. 604/30 |
| 5,906,598 A | 5/1999 | Giesler et al. |
| 5,910,110 A | 6/1999 | Bastable |
| 5,927,956 A | 7/1999 | Lim et al. |
| 5,996,634 A | 12/1999 | Dennehey et al. |
| 6,012,999 A | 1/2000 | Patterson |
| 6,129,699 A | 10/2000 | Haight et al. |
| 6,293,926 B1 | 9/2001 | Sorensen et al. |
| 6,572,349 B2 | 6/2003 | Sorensen et al. |

* cited by examiner

SURGICAL CASSETTE HAVING AN ASPIRATION PRESSURE SENSOR

This application is a continuation-in-part application of U.S. patent application Ser. No. 09/846,724, filed May 1, 2001, now U.S. Pat. No. 6,572,349 which is a continuation of U.S. patent application Ser. No. 09/437,392, filed Nov. 10, 1999, now U.S. Pat. No. 6,293,926 B1, and a continuation-in-part of U.S. patent application Ser. No. 10/153,371, filed May 28, 2002, now U.S. Pat. No. 6,902,542.

BACKGROUND OF THE INVENTION

The present invention relates generally to peristaltic pumps and more specifically to peristaltic pumps used in ophthalmic surgical equipment.

Most prior art peristaltic pumps work by compressing or squeezing a length of flexible tubing (sometimes between a fixed race) using a rotating roller head. As the roller head rotates, the rollers pinch off a portion of the tubing and push any fluid trapped in the tubing between the rollers in the direction of rotation. Peristaltic pumps are widely used in medical applications because of their predictable, constant flow properties. These prior art systems, however, typically require manual connection of the pump tube segment around the rotating roller head.

Prior art peristaltic pumps using rotating roller heads also typically impart unwanted pressure pulsations. Several pulsation damping devices have been developed to address this problem (see e.g., U.S. Pat. No. 4,921,477 (Davis)).

Accordingly, a need continues to exist for a peristaltic pump that reduces pressure pulsations and that is simpler and more economical to manufacture and use.

BRIEF SUMMARY OF THE INVENTION

The present invention improves upon prior art peristaltic pumps by providing a cassette having a molded flow channel contained on an elastomeric sheet that is bonded or mechanically attached to a rigid substrate. The cassette is used in combination with a peristaltic pump having pump head rollers that are mounted radially from the axis of rotation of the pump motor so as to compress the elastomeric flow channels against the rigid substrate during operation.

One objective of the present invention is to provide a cassette that uses molded elastomeric flow channels.

Another objective of the present invention is to provide a cassette for a peristaltic pump having radially oriented pump rollers.

Yet another objective of the present invention is to provide a cassette for a peristaltic pump having pump rollers that compress elastomeric flow channels in the cassette against a rigid substrate.

These and other advantages and objectives of the present invention will become apparent from the detailed description, drawings and claims that follow.

DETAILED DESCRIPTION OF THE INVENTION

Figure 1:
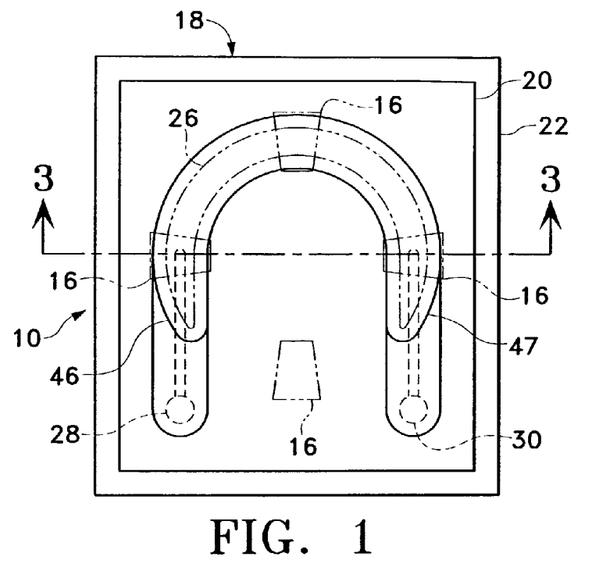
FIG. 1 is a schematic top plan view of a first embodiment of the present invention, with the motor and roller head removed for clarity.
Figure 2:
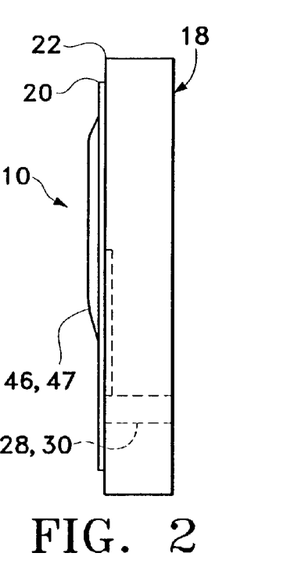
FIG. 2 is a schematic side elevational view of a first embodiment of the present invention, with the motor and roller head removed for clarity.
Figure 3:
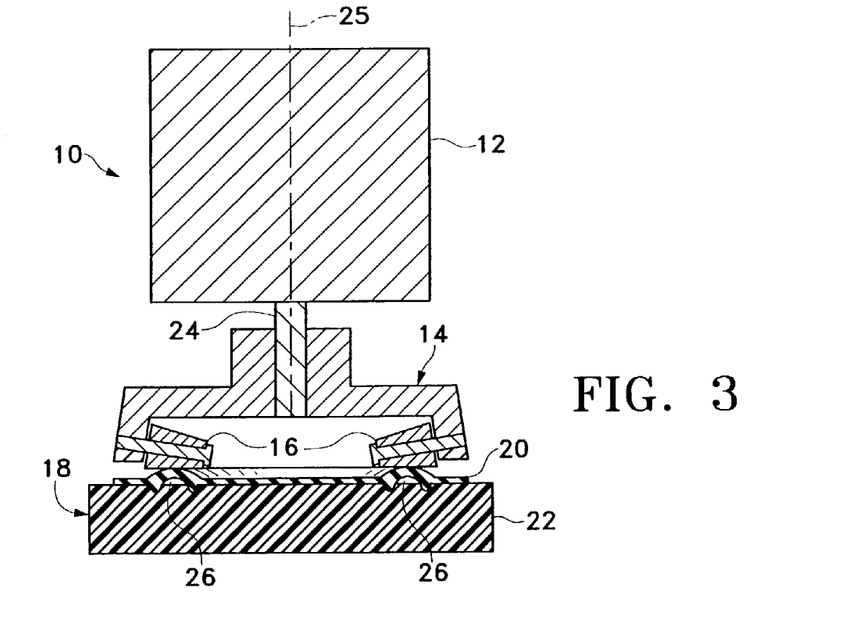
FIG. 3 is a cross-sectional view of the first embodiment of the present invention taken at line 3—3 in FIG. 1.

As best seen in FIGS. 1, 2 and 3, in a first embodiment of the present invention, pump 10 of the present invention generally includes pump motor 12, roller head 14, containing one or more rollers 16 and cassette 18 having elastomeric sheet 20 applied to the exterior of relatively rigid body or substrate 22. Pump motor 12 preferably is a stepper or D.C. servo motor. Roller head 14 is attached to shaft 24 of motor 12 so that motor 12 rotates roller head 14 in a plane generally normal to axis 25 of shaft 24, and the longitudinal axes of rollers 16 are generally radial to axis 25 of shaft 24.

Sheet 20 contains molded fluid channel 26 that is generally planar, arcuate in shape (within the plane) and having a radius approximating that of rollers 16 about shaft 24. Fluid channel 26 fluidly connects ports 28 and 30. Sheet 20 may be made of any suitably flexible, easily molded material such as silicone rubber or thermoplastic elastomer. Sheet 20 is attached or bonded to substrate 22 by any suitable technique such as adhesive, heat fusion or mechanical crimping. Substrate 22 preferably is made of a material that is rigid with respect to sheet 20, such as a rigid thermoplastic, and may be made by any suitable method, such as machining or injection molding.

In use, cassette 18 is held in close proximity to roller head 14 so that rollers 16 compress channel 26 against substrate 22 as roller head 14 rotates. The longitudinal axes of the rollers are arranged so that roller 16 contact with channel 26 is generally parallel with the plane of channel 26. Such an arrangement eliminates the need to loop a length of flexible tubing over the pump roller head and thus simplifies the loading of pump channel 26 against pump roller head 14. Rollers 16 may be tapered along their axial length to accommodate the difference in path length traveled by the inner and outer sections of rollers 16 as roller head 14 rotates. Unwanted pressure pulsations could be minimized by providing channel transition regions 46 and 47 having internal cross-sections that taper from zero to the full cross-section of channel 26. These regions minimize the abrupt change in displaced volume as rollers 16 transition on or off of channel 26.

Figure 4:
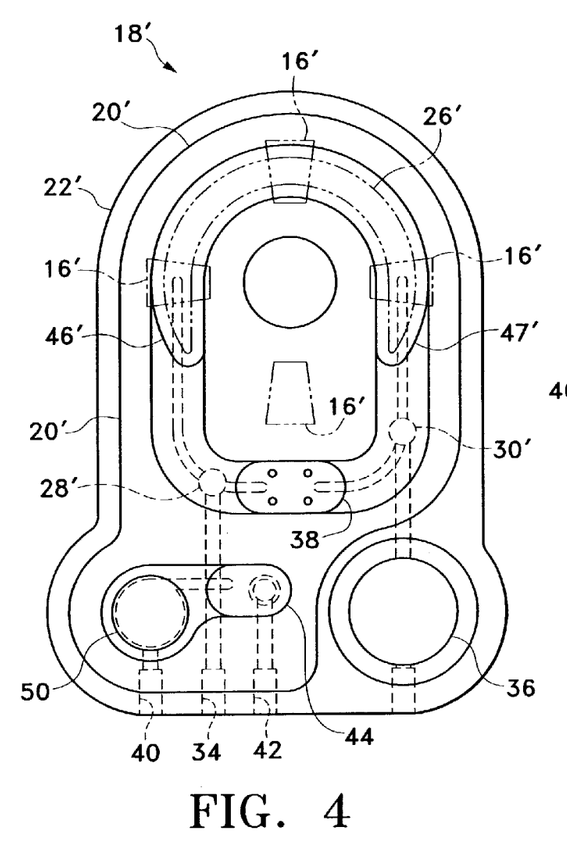
FIG. 4 is a schematic top plan view of a second embodiment of the present invention, with the motor and roller head removed for clarity.
Figure 5:
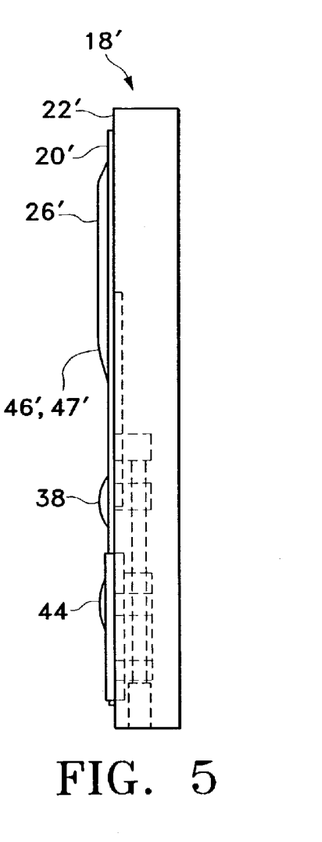
FIG. 5 is a schematic side elevational view of a second embodiment of the present invention, with the motor and roller head removed for clarity.
Figure 6:
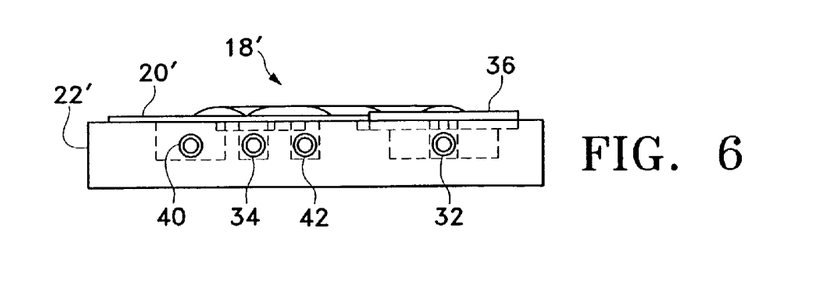
FIG. 6 is a schematic front elevational view of a second embodiment of the present invention, with the motor and roller head removed for clarity.

As best seen in FIGS. 4–6, in a second embodiment of the present invention, cassette 18' may contain additional fluid channels that provide control of irrigation fluid as well as aspiration fluid. For example, cassette 18' may contain aspiration inlet port 32 and aspiration outlet port 34 that are connected through channel 26'. Upstream of port 32, cassette 18' may contain aspiration pressure sensor interface 36, which may be any of a variety of non-invasive pressure sensors such as those disclosed in U.S. Pat. No. 5,910,110 (Bastable) and U.S. Pat. No. 5,470,312 (Zanger, et al.), the entire contents of which being incorporated herein by reference. Cassette 18' may also contain a vent pinch valve site 38 for allowing the venting of any vacuum from channel 26'. Irrigation fluid enters cassette 18' through port 40 and exits cassette 18' through port 42 and is controlled by valve or pinch valve site 44, which may be actuated by a plunger (not shown). Vent 38 may be operated in a similar method. In addition, between port 40 and irrigation pinch valve site 44, cassette 18' may contain irrigation pressure interface 50. Pressure interface 50 may be made from a thin molded membrane contained within elastomeric sheet 20' over a fluid chamber (not shown) contained within substrate 22'. Such an interface allows detection of irrigation pressure in a non-invasive manner using a surface contact pressure transducer or calibrated load cell.

Figure 7:
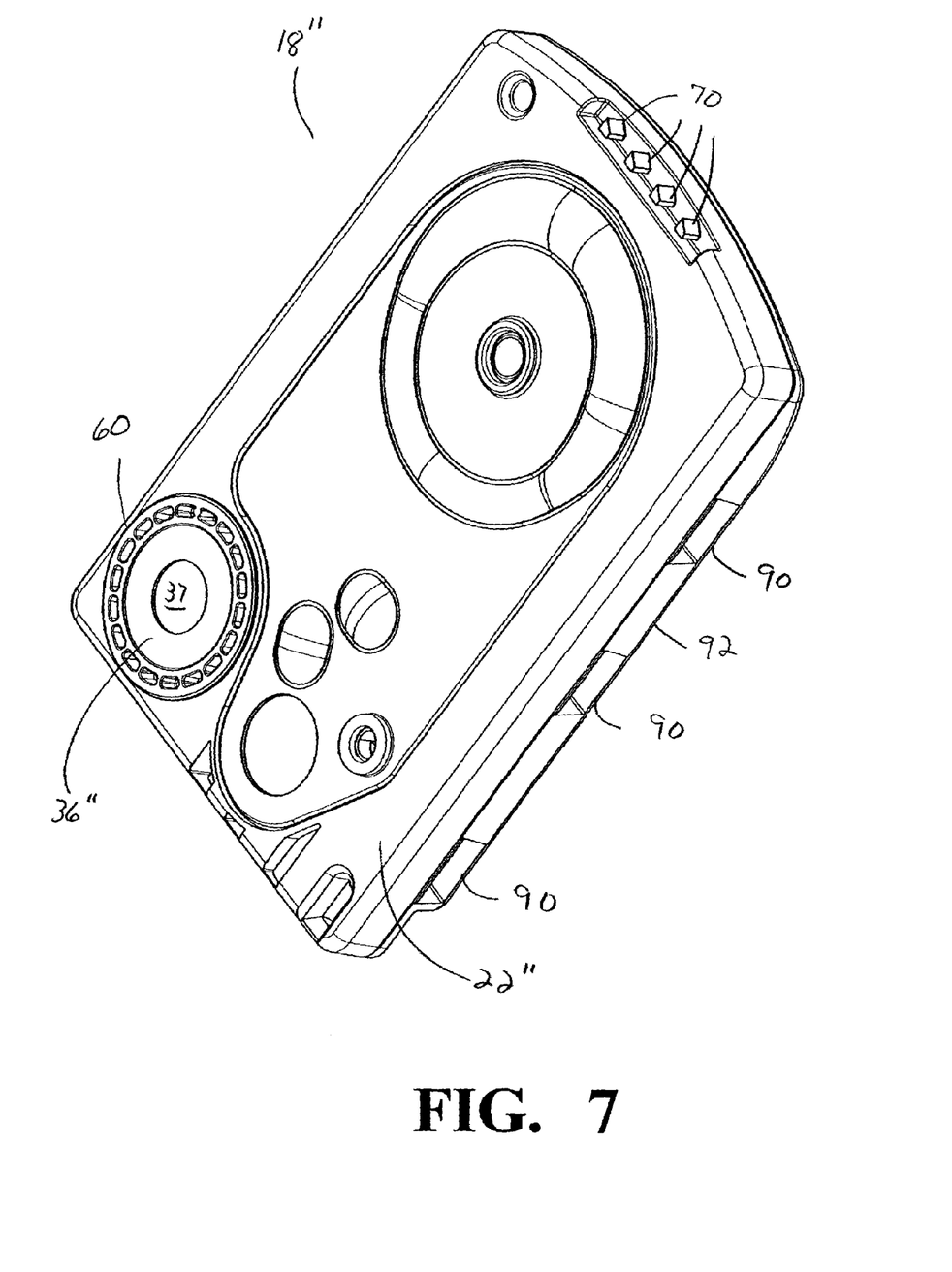
FIG. 7 is a perspective view of a third embodiment of the cassette of the present invention.
Figure 9:
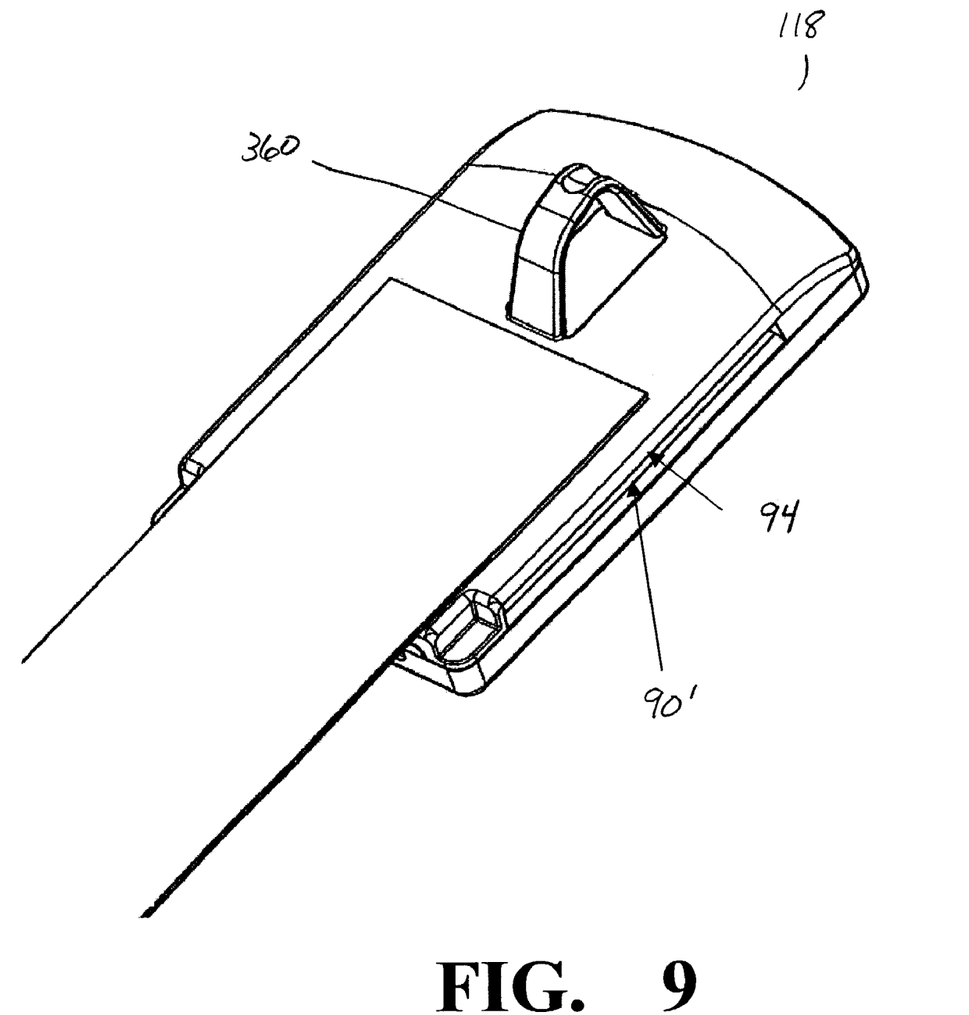
FIG. 9 is a perspective view of a fourth embodiment of the cassette of the present invention.
Figure 10:
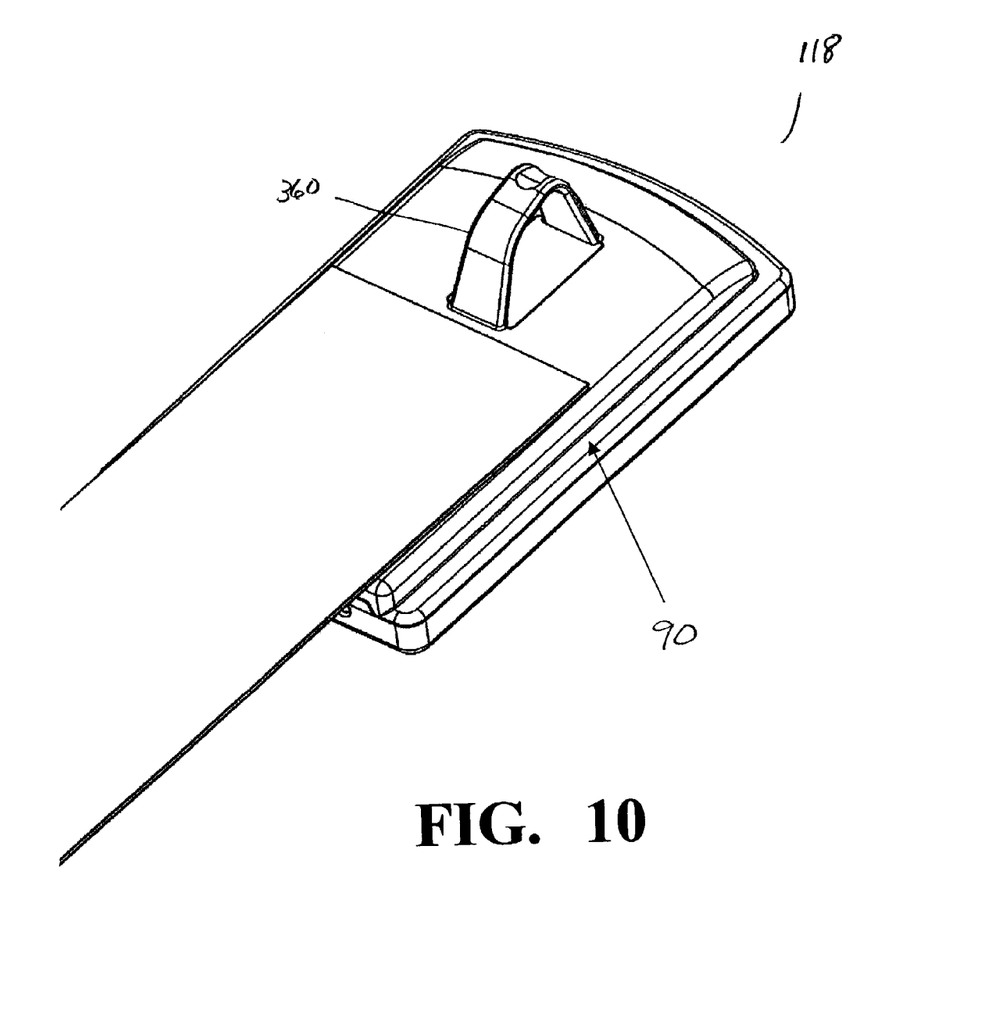
FIG. 10 is a perspective view of a fifth embodiment of the cassette of the present invention.

As best seen in FIG. 7, cassette 18" of the present invention contains aspiration pressure sensor interface 36". Interface 36" may consist of thin diaphragm 37 preferably made of metal or rigid plastic. An external loadcell (not shown) located on console 80 is used to deflect diaphragm 37 to a predetermined initial force load. Changes in pressure on the internal side of diaphragm 37 opposite the loadcell will cause a change in force on the loadcell that can be correlated to the pressure level on interface 36". The inventors have discovered that forces on cassette 18" during use can cause flexing of substrate 22". Such flexing can cause inaccurate reading from the load cell used in conjunction with pressure sensor interface 36". In order to minimize such inaccuracies, substrate 22" contains a raised boss 60 around pressure sensor interface 36". When substrate 22" is clamped in place against a rigid mounting member (not shown) on console 80, boss 60 helps to stabilize the area around pressure sensor interface 36" and isolate pressure sensor interface 36" from forces acting on other regions of substrate 22". In addition, cassette 18" may contain one or more plurality of latching surfaces 90 per side that cooperate with a latching mechanism, such as the latching mechanism described in commonly-owned U.S. patent application Ser. No. 10/132,797, filed Apr. 25, 2002, to assist in holding cassette 18" firmly within console 80 further reducing the possibility of flexing of cassette 18". Latching surfaces 90 preferably are located along sides 92 of substrate 22" and preferably, are formed as indentations within sides 92 of substrate 22". Such a construction helps to prevent the possibility of the latching mechanism capturing the finger of a user. Alternatively, as shown in FIGS. 9–10, cassette 118 can have continuous latching surfaces 90' with (FIG. 9) or without (FIG. 10) finger pinch protective cover 94. Cassette 118 preferably has handle 360 that is aligned near the axis of the pump roller head. Such a construction eases the insertion of cassette 118 into the latching mechanism.

Figure 8:
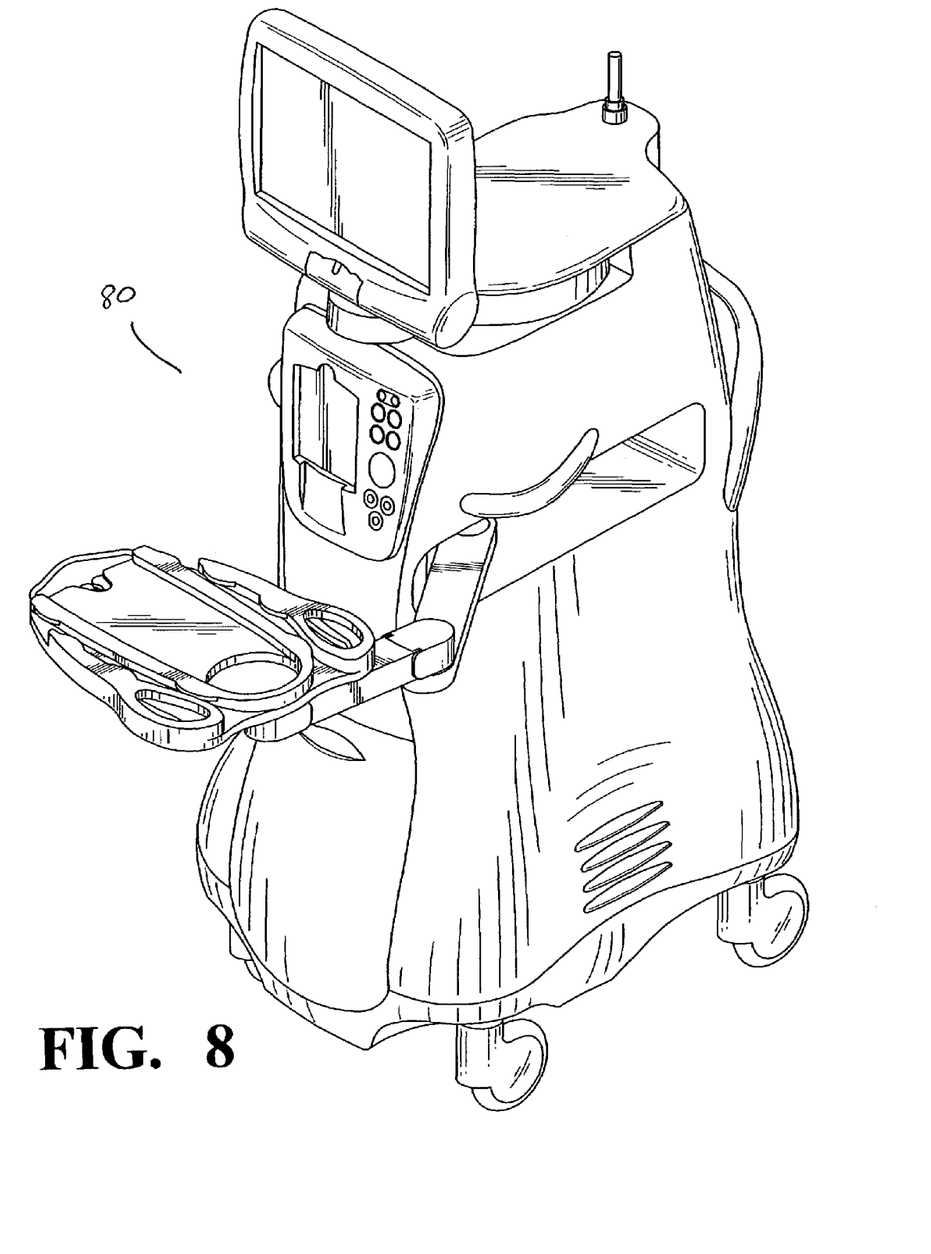
FIG. 8 is a perspective view of a surgical console that may be used with the present invention.

Cassette 18" that may be used with pump 10 of the present invention may also contain a plurality of identifying tabs 70 projecting from housing substrate 22". Tabs 70 may be generally of the shape described in U.S. Pat. No. 6,059,544 (Jung, et al.) and may be of variable opaqueness, from completely opaque to partially translucent to relatively clear. The opaqueness of tabs 70 may be used by console 80 (as seen in FIG. 8) to identify the particular cassette 18" being used from a variety of suitable cassette 18" in a manner similar to that disclosed in U.S. Pat. No. 6,059,544 (Jung, et al.), the entire contents of which being incorporated herein by reference.

Figure 11:
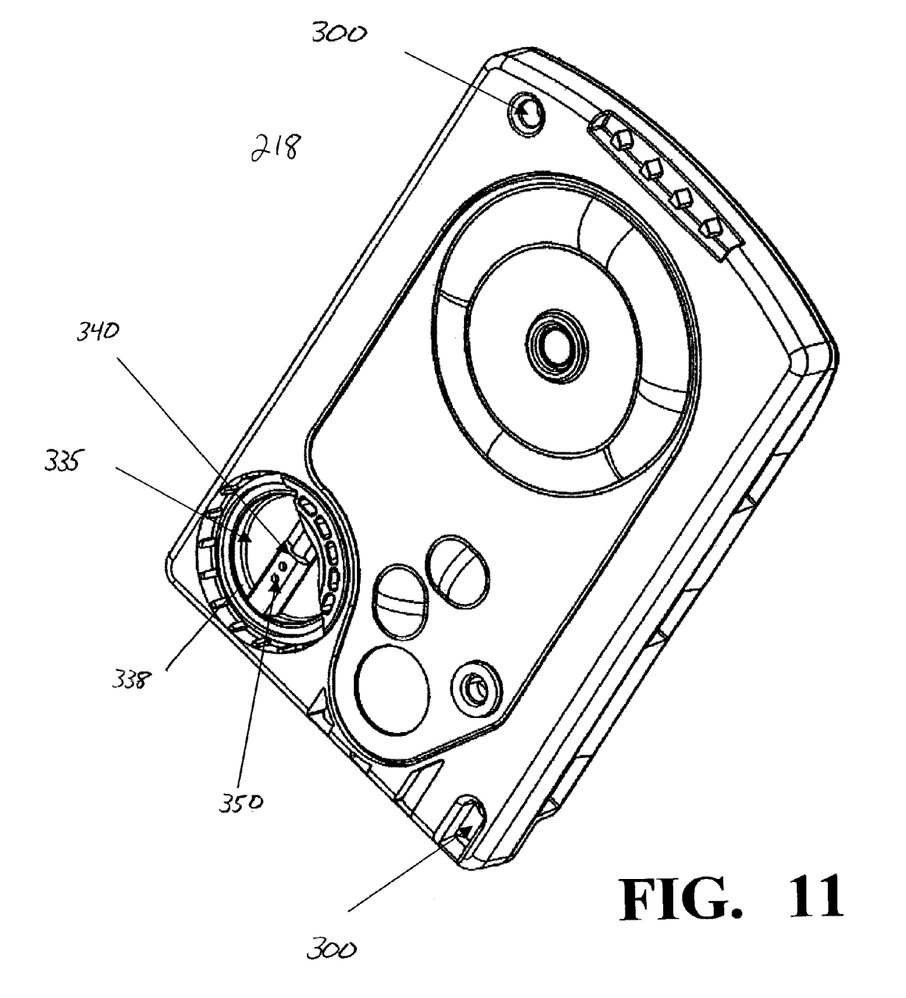
FIG. 11 is a perspective view of the cassette of the present invention.

As best seen in FIG. 11, cassette 218 may contain one or more alignment features, such as indentations 300 that match corresponding alignment features (not shown) on console 80. One skilled in the art will recognize that instead of indentation 300, protrusions (not shown) may be used alternatively. Indentations 80 assure that cassette 218 is located properly within console 80, rotationally, vertically and horizontally. Indentations 80 may be located on either side of cassette 218.

In addition, pressure sensor well 335 has aspiration exit port 340 located above bottom 338 of well 335. Such a construction allows any solid material flowing into well 335 through port 340 to precipitate down to bottom 338 of well 335. Port 340 is also located in the middle of well 335 so as not to draw precipitated material on bottom 338 into port 340 during reverse flow situations, such as venting or reflux. Cassette 218 may contain one or more auxiliary vent port(s) 350 that provides redundant venting paths in case port 340 becomes clogged.

This description is given for purposes of illustration and explanation. It will be apparent to those skilled in the relevant art that modifications may be made to the invention as herein described without departing from its scope or spirit.

We claim:

1. A cassette, comprising:
    a) a body having an exterior;
    b) a relatively flexible sheet attached to the body, the sheet containing at least one molded fluid channel, the fluid channel projecting outwardly from the exterior of the body;
    c) an aspiration pressure sensor interface on the exterior of the body, the interface having a well, the well having an outlet;
    d) a first aspiration exit port in the well, the aspiration exit port being located above a bottom of the well; and
    e) at least one vent port in the pressure sensor well, the vent port providing a second aspiration exit port into the well.

2. The cassette of claim 1 wherein the sheet comprises a molded aspiration fluid channel and a molded irrigation fluid channel.

3. The cassette of claim 1 wherein the sheet comprises a flexible, easily molded material.

4. The cassette of claim 3 wherein the sheet comprises silicone rubber or thermoplastic elastomer.

5. The cassette of claim 1 wherein the fluid channel is planar.

6. The cassette of claim 1 wherein the fluid channel has at least one transition region wherein the cross-sectional area of the fluid channel tapers.

7. The cassette of claim 1 wherein the fluid channel has at least one pinch valve site.

8. The cassette of claim 1 wherein the cassette further comprises a plurality of identifying tabs projecting from the exterior of the body.

9. A cassette, comprising:
    a) a body having an exterior;
    b) a relatively flexible sheet attached to the body, the sheet containing at least one molded fluid channel, the fluid channel projecting outwardly from the exterior of the body;
    c) an aspiration pressure sensor interface on the exterior of the body;

d) a raised boss around the pressure sensor interface;
e) a pressure sensor well and an aspiration exit port located above a bottom of the well; and
f) at least one vent port in the pressure sensor well.

10. The cassette of claim 9 wherein the sheet comprises a molded aspiration fluid channel and a molded irrigation fluid channel.

11. The cassette of claim 9 wherein the sheet comprises a flexible, easily molded material.

12. The cassette of claim 11 wherein the sheet comprises silicone rubber or thermoplastic elastomer.

13. The cassette of claim 9 wherein the fluid channel is planar.

14. The cassette of claim 9 wherein the fluid channel has at least one transition region wherein the cross-sectional area of the fluid channel tapers.

15. The cassette of claim 9 wherein the fluid channel has at least one pinch valve site.

16. The cassette of claim 9 wherein the cassette further comprises a plurality of identifying tabs projecting from the exterior of the body.

17. A cassette, comprising:
a) a body having an exterior;
b) a relatively flexible sheet attached to the body, the sheet containing at least one molded fluid channel, the fluid channel projecting outwardly from the exterior of the body and containing at least one pinch valve site;
c) an aspiration pressure sensor interface on the exterior of the body;
d) a raised boss around the pressure sensor interface;
e) a plurality of identifying tabs projecting from the exterior of the body;
f) a pressure sensor well and an aspiration exit port located above a bottom of the well; and
g) at least one vent port in the pressure sensor well.

18. The cassette of claim 17 wherein the sheet comprises a molded aspiration fluid channel and a molded irrigation fluid channel.

19. The cassette of claim 17 wherein the sheet comprises a flexible, easily molded material.

20. The cassette of claim 19 wherein the sheet comprises silicone rubber or thermoplastic elastomer.

21. The cassette of claim 17 wherein the fluid channel is planar.

22. The cassette of claim 17 wherein the fluid channel has at least one transition region wherein the cross-sectional area of the fluid channel tapers.

23. A cassette, comprising:
a) a body having an exterior, the exterior having sides;
b) a relatively flexible sheet attached to the body, the sheet containing at least one molded fluid channel, the fluid channel projecting outwardly from the exterior of the body;
c) an aspiration pressure sensor interface on the exterior of the body;
d) a plurality of latching surfaces formed in the sides of the body;
e) a pressure sensor well and an aspiration exit port located above a bottom of the well; and
f) at least one vent port in the pressure sensor well.

24. The cassette of claim 23 wherein the sheet comprises a molded aspiration fluid channel and a molded irrigation fluid channel.

25. The cassette of claim 23 wherein the sheet comprises a flexible, easily molded material.

26. The cassette of claim 25 wherein the sheet comprises silicone rubber or thermoplastic elastomer.

27. The cassette of claim 23 wherein the fluid channel is planar.

28. The cassette of claim 23 wherein the fluid channel has at least one transition region wherein the cross-sectional area of the fluid channel tapers.

29. The cassette of claim 23 wherein the fluid channel has at least one pinch valve site.

30. The cassette of claim 23 wherein the cassette further comprises a plurality of identifying tabs projecting from the exterior of the body.

31. A cassette, comprising:
a) a body having an exterior, the exterior having sides;
b) a relatively flexible sheet attached to the body, the sheet containing at least one molded fluid channel, the fluid channel projecting outwardly from the exterior of the body and containing at least one pinch valve site;
c) an aspiration pressure sensor interface on the exterior of the body;
d) a raised boss around the pressure sensor interface;
e) a plurality of identifying tabs projecting from the exterior of the body;
f) a plurality of latching surfaces formed in the sides of the body;
g) a pressure sensor well and an aspiration exit port located above a bottom of the well; and
h) at least one vent port in the pressure sensor well.

32. The cassette of claim 31 wherein the sheet comprises a molded aspiration fluid channel and a molded irrigation fluid channel.

33. The cassette of claim 31 wherein the sheet comprises a flexible, easily molded material.

34. The cassette of claim 33 wherein the sheet comprises silicone rubber or thermoplastic elastomer.

35. The cassette of claim 31 wherein the fluid channel is planar.

36. The cassette of claim 31 wherein the fluid channel has at least one transition region wherein the cross-sectional area of the fluid channel tapers.

37. A cassette, comprising:
a) a body having an exterior;
b) a relatively flexible sheet attached to the body, the sheet containing at least one molded fluid channel, the fluid channel projecting outwardly from the exterior of the body;
c) an aspiration pressure sensor interface on the exterior of the body, the interface having a well, the well having an outlet;
d) a plurility of alignment features in the exterior;
e) a pressure sensor well and a first aspiration exit port located above a bottom of the well; and
f) at least one vent port in the pressure well, the vent port providing a second aspiration exit port into the well.

38. The cassette of claim 37 wherein the sheet comprises a molded aspiration fluid channel and a molded irrigation fluid channel.

39. The cassette of claim 37 wherein the sheet comprises a flexible, easily molded material.

40. The cassette of claim 39 wherein the sheet comprises silicone rubber or thermoplastic elastomer.

41. The cassette of claim 37 wherein the fluid channel is planar.

42. The cassette of claim 37 wherein the fluid channel has at least one transition region wherein the cross-sectional area of the fluid channel tapers.

43. The cassette of claim 37 wherein the fluid channel has at least one pinch valve site.

44. The cassette of claim 37 wherein the cassette further comprises a plurality of identifying tabs projecting from the exterior of the body.

\* \* \* \* \*